(12) United States Patent
Kim et al.

(10) Patent No.: US 11,701,313 B2
(45) Date of Patent: Jul. 18, 2023

(54) TOOTHPASTE COMPOSITION

(71) Applicant: LG Household & Health Care Ltd., Seoul (KR)

(72) Inventors: Ji Young Kim, Seoul (KR); Seongwoo Bak, Seoul (KR); Won Ho Ha, Seoul (KR)

(73) Assignee: LG Household & Health Care Ltd.

( * ) Notice: Subject to any disclaimer, the term of this patent is extended or adjusted under 35 U.S.C. 154(b) by 0 days.

(21) Appl. No.: 17/053,974

(22) PCT Filed: Mar. 27, 2020

(86) PCT No.: PCT/KR2020/004266
§ 371 (c)(1),
(2) Date: Nov. 9, 2020

(87) PCT Pub. No.: WO2020/197342
PCT Pub. Date: Oct. 1, 2020

(65) Prior Publication Data
US 2021/0236400 A1    Aug. 5, 2021

(30) Foreign Application Priority Data

| Mar. 28, 2019 | (KR) | 10-2019-0036186 |
| Mar. 28, 2019 | (KR) | 10-2019-0036187 |
| Mar. 28, 2019 | (KR) | 10-2019-0036188 |

(51) Int. Cl.
| A61K 8/25 | (2006.01) |
| A61K 8/02 | (2006.01) |
| A61K 8/24 | (2006.01) |
| A61Q 11/00 | (2006.01) |
| A61K 8/22 | (2006.01) |
| A61K 8/60 | (2006.01) |
| A61K 8/81 | (2006.01) |
| A61K 8/86 | (2006.01) |

(52) U.S. Cl.
CPC .............. *A61K 8/25* (2013.01); *A61K 8/0241* (2013.01); *A61K 8/22* (2013.01); *A61K 8/24* (2013.01); *A61K 8/602* (2013.01); *A61K 8/608* (2013.01); *A61K 8/8176* (2013.01); *A61K 8/86* (2013.01); *A61Q 11/00* (2013.01); *A61K 2800/48* (2013.01)

(58) Field of Classification Search
CPC .................................. A61K 8/00; A61Q 11/00
USPC ....................................................... 424/49, 57
See application file for complete search history.

(56) References Cited

U.S. PATENT DOCUMENTS

| 4,353,890 A | 10/1982 | Scott |
| 5,085,853 A | 2/1992 | Williams et al. |
| 5,302,374 A | 4/1994 | Wagner |
| 6,162,418 A | 12/2000 | Randive et al. |
| 6,506,366 B1 | 1/2003 | Leinen et al. |
| 2003/0124067 A1 | 7/2003 | Yue et al. |
| 2008/0248072 A1* | 10/2008 | Glandorf .................. A61K 8/02 424/49 |
| 2010/0040562 A1 | 2/2010 | Frost et al. |
| 2010/0135921 A1* | 6/2010 | Hughes .................. A61Q 11/00 424/49 |
| 2011/0189111 A1 | 8/2011 | Crawshaw et al. |
| 2011/0317701 A1 | 12/2011 | Yamato et al. |
| 2016/0151255 A1 | 6/2016 | You et al. |
| 2017/0119634 A1 | 5/2017 | Zeng et al. |
| 2019/0209448 A1* | 7/2019 | Dogu ..................... A61K 8/345 |

FOREIGN PATENT DOCUMENTS

| CN | 1592605 A | 3/2005 |
| CN | 105534875 A | 5/2016 |
| CN | 105792798 A | 7/2016 |
| CN | 107625659 A | 1/2018 |
| JP | H10182389 A | 7/1998 |
| JP | 2001039843 A | 2/2001 |
| JP | 2003089627 A | 3/2003 |
| JP | 2005510538 A | 4/2005 |
| JP | 6075416 B2 | 2/2017 |
| JP | 2018104417 A | 7/2018 |
| KR | 20010075492 A | 8/2001 |

(Continued)

OTHER PUBLICATIONS

International Search Report for PCT/KR2020/004266 dated Jun. 24, 2020; 3 pages.

(Continued)

*Primary Examiner* — Walter E Webb
(74) *Attorney, Agent, or Firm* — Lerner David LLP

(57) ABSTRACT

A toothpaste composition includes a structurant and a thickener, wherein the toothpaste composition has a predetermined viscosity and phase angle by using the structurant instead of reducing the content of a thickener, and thereby has an improved release property during use while maintaining a shape retention property of the toothpaste, and has an improved feeling of refreshment, flavor releasing power, cleaning power, and stain removal power. Further, provided is a toothpaste composition including a chelating agent containing phosphate and silica, wherein the chelating agent is supersaturated to precipitate phosphate to provide strong cleaning power, a whitening effect, a stain removal effect, and a crunchy sensation. Further, provided is a toothpaste composition including a peroxide, a thickener, and a spreading agent, wherein the peroxide and the thickener are separated from each other, providing excellent sense of use, stability, and a whitening effect in an anhydrous state.

4 Claims, 3 Drawing Sheets

(56) References Cited

FOREIGN PATENT DOCUMENTS

| KR | 20050023598 A | 3/2005 |
| KR | 20050048853 A | 5/2005 |
| KR | 20070028512 A | 3/2007 |
| KR | 20080107799 A | 12/2008 |
| KR | 20140146983 A | 12/2014 |
| KR | 20160131488 A | 11/2016 |
| KR | 102246287 B1 | 4/2021 |
| WO | 9804234 A1 | 2/1998 |
| WO | 0019971 A1 | 4/2000 |
| WO | 03045344 A2 | 6/2003 |
| WO | WO2018065264 * | 4/2018 ............... A61K 8/25 |

OTHER PUBLICATIONS

GNPD. "Whitening Toothpaste" Colgate—Palmolive, Catergory: Oral Hygiene, Oct. 2003, pp. 1-2. https://www.gnpd.com.
Extended European Search Report including Written Opinion for Application No. 20779633.5 dated Mar. 7, 2023, pp. 1-9.
Cosdna, "Crest Fluoride Anticavity Toothpaste", https://cosdna.com/chs/ cosmetic_0db916583.html, (Apr. 2006). 2 pgs.

* cited by examiner

[FIG. 1]
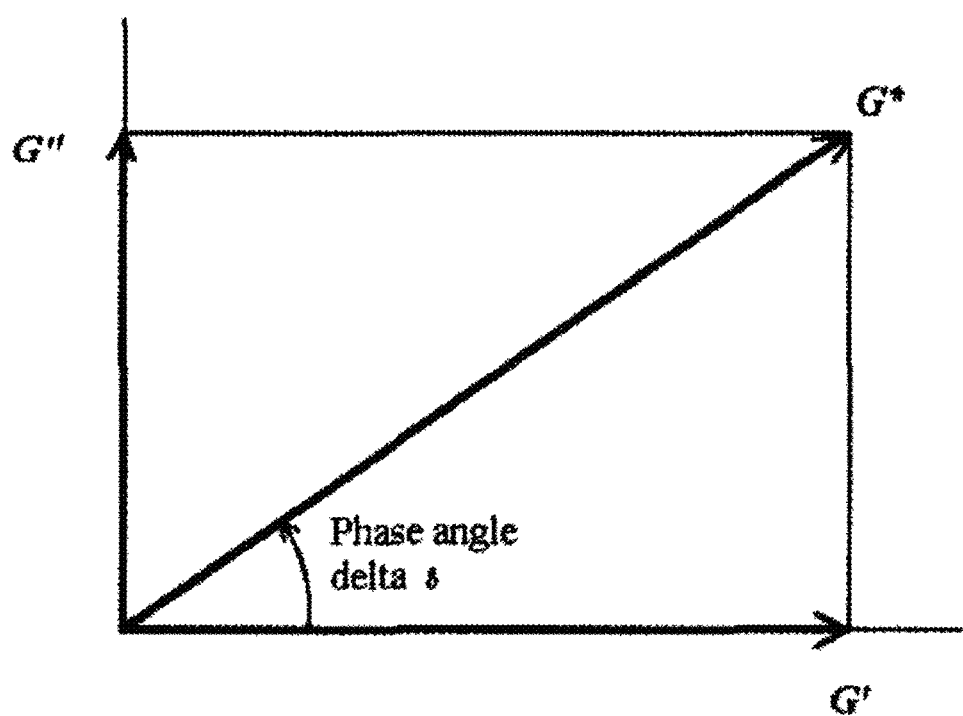

[FIG. 2]
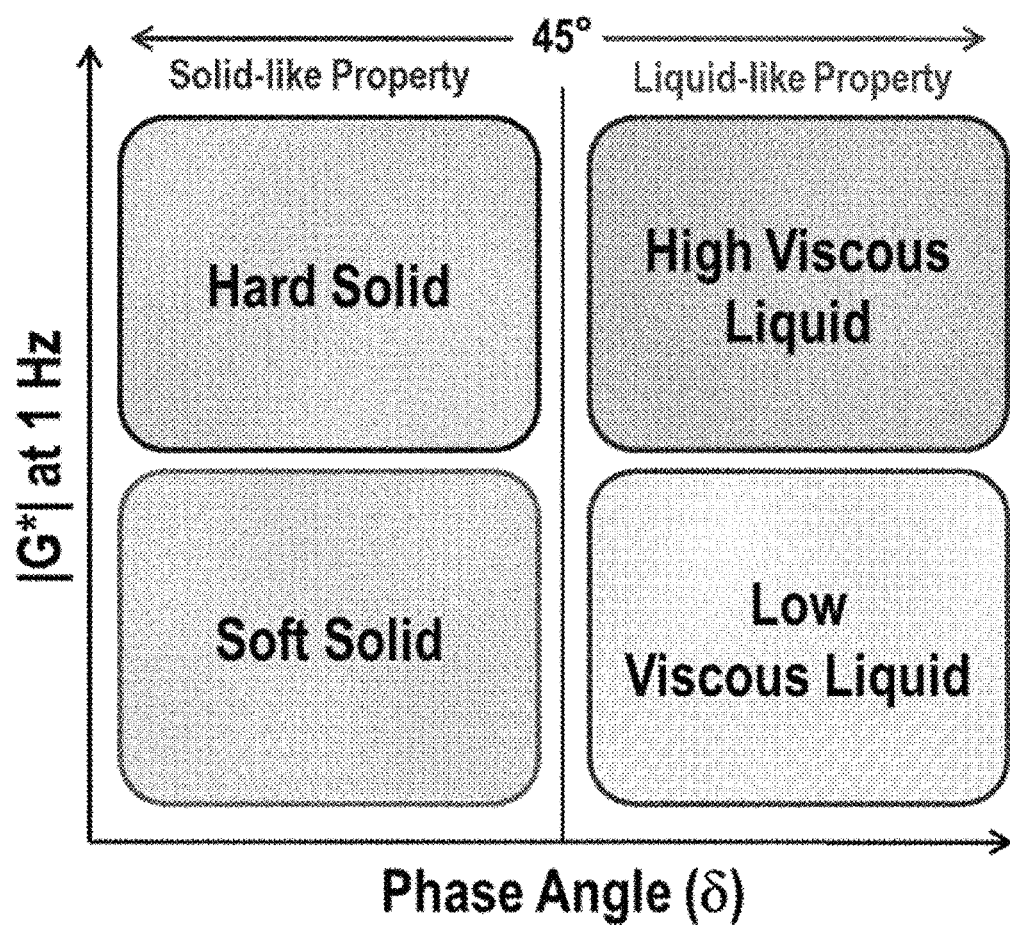

[FIG. 3]
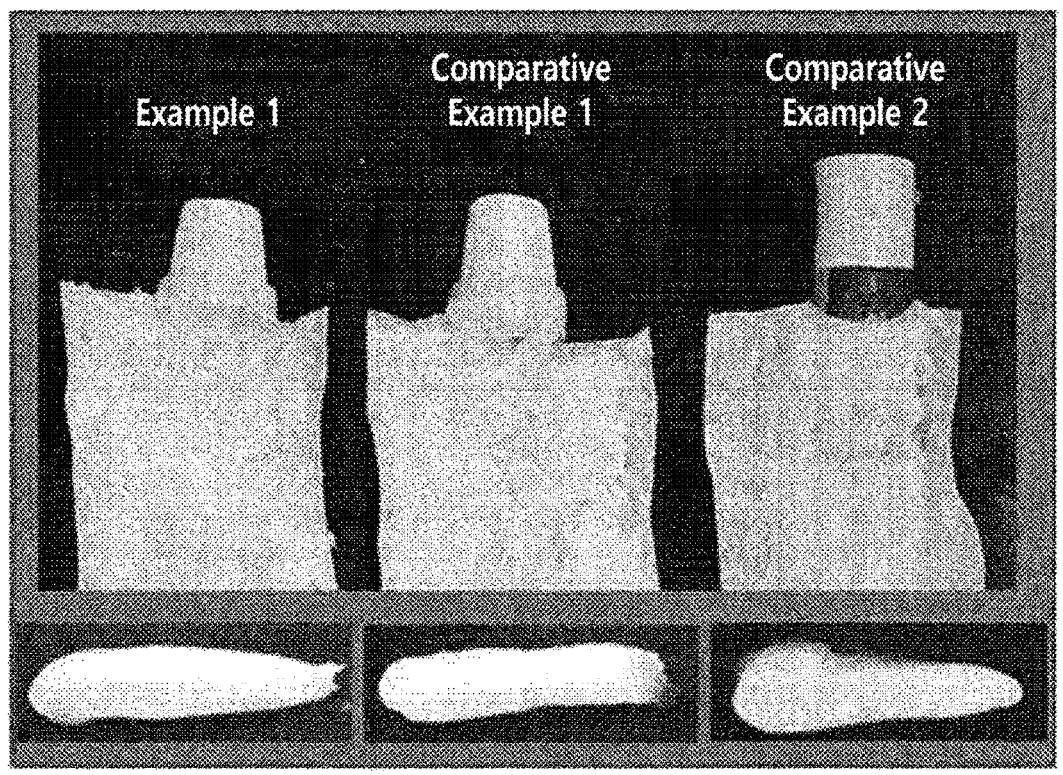

TOOTHPASTE COMPOSITION

CROSS-REFERENCE TO RELATED APPLICATIONS

This application is a national phase entry under 35 U.S.C. § 371 of International Application No. PCT/KR2020/004266, filed Mar. 27, 2020, which claims priority to Korean Patent Application Nos. 10-2019-0036188, 10-2019-0036187 and 10-2019-0036186 filed Mar. 28, 2019.

TECHNICAL FIELD

The present invention relates to a toothpaste composition including a structurant and a thickener, and specifically, a toothpaste composition having an improved shape retention property, release property when used, feeling of refreshment, flavor releasing power, cleaning power, and stain-removing power.

Further, the present invention relates to a toothpaste composition having an improved whitening effect and sense of use, specifically, a toothpaste composition including silica and a chelating agent containing phosphate, wherein the chelating agent is supersaturated to precipitate phosphate, and particles of the precipitated phosphate realize a strong cleaning power, a whitening effect, stain removal, and a crunchy sensation when used.

Further, the present invention relates to a toothpaste composition including a peroxide, a thickener, and a spreading agent, wherein the peroxide and the thickener are separated from each other, and specifically, a toothpaste composition having excellent sense of use, stability, and a whitening effect even in an anhydrous state.

BACKGROUND ART

A release property of toothpastes is important at the time of use for rapid delivery of active ingredients. An excellent release property has a great influence on the rapid delivery of the active ingredients supported in the toothpaste, foam generation, and consumers' sense of use.

In addition, existing common toothpastes are blended with xanthan gum, etc. to prepare a thickening system, so that the toothpaste is allowed to be discharged from a container such as a tube. In other words, a thickener or a binder is included to build viscosity of the toothpaste. In existing toothpaste compositions, the thickener or the binder is included at a high concentration.

However, when the thickening force is strong, the thickener creates a binding force between the components throughout the toothpaste, and this causes a problem in that the toothpaste stuck together is not easily released by saliva or tooth brushing. For this reason, liquid toothpaste compositions have been developed. However, liquid toothpaste compositions have a disadvantage of easily flowing away due to low viscosity, and thus are widely used as mouthwashes that perform functions of inhibiting oral bacteria and removing bad breath. However, due to the lack of cleaning ingredients and easy flowing, they do not exert sufficient brushing effects such as removal of plaque and removal of oral bacteria in the mouth (Korean Patent Application No. 2001-7004081).

With the growing interest in tooth whitening, there are many kinds of whitening toothpastes on the market. However, even though the toothpastes include an effective whitening agent, the toothpastes are used for a short time of 1 minute to 3 minutes, and thus it is necessary in terms of sense of use and effect to rapidly release the active ingredient or flavor. For the tooth whitening, staining materials on the tooth surface or staining materials between the teeth must be removed.

Discoloration on the tooth surface is known to result from deposition of food-derived pigments (tea, coffee, red wine, etc.) as extrinsic stains, discoloration due to Maillard reaction by denaturation of glycoproteins in the saliva covering the dental surface, discoloration by sulfur-containing amino acids or metals, or discoloration of double bond moieties in proteins.

However, although toothpastes containing particles have been developed in order to provide strong cleaning power and a feeling of cleaning, problems of unsatisfactory effects, safety, and environmental pollution have been raised.

Further, since a toothpaste has a foaming agent, an abrasive, and an active ingredient, it has basic properties of providing cleaning power and a feeling of refreshment when used with a toothbrush. However, except for chemical bleaching by hydrogen peroxide, discoloration on the tooth surface is difficult to remove.

Generally, consumers want to receive whitening effects only with their daily brushing for their convenience. Whitening toothpastes should be able to break double bonds of staining materials by penetrating the whitening component to the dentin. A substance having this effect is peroxide, which has a low molecular weight and is decomposed into water and oxygen.

However, hydrogen peroxide is highly reactive with water, and thus it is easily decomposed in water and has poor compatibility with other components of toothpastes such as polymers, abrasives, fluoride, foaming agents, etc. In particular, toothpastes containing hydrogen peroxide have a disadvantage in that an abrasive cannot be added together therewith, and therefore, it is difficult to achieve a synergistic effect of two mechanisms in the whitening effect. For this reason, toothpastes containing water as a solvent and a large amount of hydrogen peroxide while having high viscosity suitable for tube toothpaste, fluoride, a foaming agent, an abrasive, a flavor, etc. have poor stability of peroxide at a high temperature over time, and as a result, phase separation of hydrogen peroxide occurs, and thus its commercialization is difficult.

DISCLOSURE

Technical Problem

There have been many efforts to solve the problems of the conventional art, and as a result, the present inventors found that when a structurant is used instead of reducing the content of a thickener, a toothpaste composition has an improved release property during use while maintaining a shape retention property by having a predetermined viscosity and phase angle, and the toothpaste composition has excellent cleaning power and stain-removing power, thereby completing the toothpaste composition of the present invention.

The present inventors also found that when a toothpaste composition includes a chelating agent with phosphate supersaturation, the toothpaste composition may have strong cleaning power, a whitening effect, an excellent stain removal effect, and a crunchy sensation when used due to the precipitated phosphate particles, thereby completing the toothpaste composition of the present invention.

The present inventors also found that when a toothpaste composition includes a peroxide, a thickener, and a spreading agent, wherein the peroxide and the thickener are separated from each other, it may have excellent sense of use and a whitening effect in spite of using a foaming agent, an abrasive, etc. having high compatibility with hydrogen peroxide in an anhydrous base, thereby completing the toothpaste composition of the present invention.

Technical Solution

An object of the present invention is to provide a toothpaste composition including a structurant and a thickener.

Another object of the present invention is to provide a toothpaste composition including silica and a chelating agent containing phosphate, wherein the chelating agent is supersaturated to precipitate phosphate, and the amount of the precipitated phosphate is 2% to 10% based on the total weight of the toothpaste composition.

Still another object of the present invention is to provide a toothpaste composition including a peroxide, a thickener, and a spreading agent.

Still another object of the present invention is to provide a toothpaste composition including a peroxide and a thickener, wherein the peroxide and the thickener are separated from each other.

Advantageous Effects

The toothpaste composition according to the present invention has a predetermined viscosity and phase angle by using a structurant instead of reducing the content of a thickener, and thereby has an improved release property during use while maintaining a shape retention property of the toothpaste, as well as excellent cleaning power and stain removal power.

Further, the toothpaste composition according to the present invention includes a chelating agent with phosphate supersaturation, and thereby has a crunchy sensation due to the supersaturated and precipitated phosphate particles, as well as strong cleaning power, an excellent whitening effect, and a stain removal effect.

Further, the toothpaste composition according to the present invention includes a peroxide, a thickener, and a spreading agent, in which the peroxide and the thickener are separated from each other, and thereby has an excellent whitening effect due to more rapid decomposition of hydrogen peroxide in an anhydrous state even though a foaming agent, an abrasive, etc. having high compatibility with hydrogen peroxide are used, and also has excellent sense of use and stability.

BRIEF DESCRIPTION OF DRAWINGS

FIG. 1 shows a value of loss tangent (tan δ) indicating a ratio of viscosity to elasticity (energy loss/energy stored).

FIG. 2 shows classification of physical properties according to the phase angle.

FIG. 3 shows a comparison of toothpaste tubes cut in half after the toothpaste in the tube was stored for 4 weeks in a 50° C. incubator.

BEST MODE FOR CARRYING OUT THE INVENTION

Hereinafter, the present invention will be described in more detail.

Meanwhile, each description and embodiment disclosed in this disclosure may also be applied to other descriptions and embodiments. That is, all combinations of various elements disclosed in this disclosure fall within the scope of the present invention. Further, the scope of the present invention is not limited by the specific description below.

Further, those skilled in the art will recognize, or will be able to ascertain using no more than routine experimentation, many equivalents to the specific embodiments of the invention described herein. Further, these equivalents should be interpreted to fall within the present invention.

To solve the above problems, an aspect of the present invention provides a toothpaste composition including a structurant and a thickener.

As used herein, the term "structurant" means a material that aggregates toothpaste components by a polymer network due to strong interaction between polymers themselves, and has high gelation ability but relatively low interaction with other toothpaste components including water, such that its structure is easily collapsed by saliva, wet toothpaste before use, or an external force such as brushing, etc., and as a result, its release property is strengthened. The structurant is to make up for disadvantages of using the thickener, and it may be included to improve the release property and to maintain the shape retention property, instead of the thickener.

The structurant of the present invention may be one or more components selected from the group consisting of carrageenan and carbomer, but is not limited thereto.

As used herein, the term "phase angle" refers to an angle corresponding to a tangent value of a trigonometric function for 'viscosity/elasticity', and is specifically as follows.

In a dynamic oscillatory shear test, w represents oscillation frequency, δ represents a phase lag between stress and strain, G' (an elastic modulus with no energy loss due to no phase lag between stress and strain) represents an elastic component of a material and is a measure of the stored energy, and G" represents viscosity of the material and is a measure of the energy lost as heat. In particular, G"/G', a ratio of G" to G', is called loss tangent (tan δ), indicating a ratio of viscosity to elasticity of the material (energy loss/energy stored), which is also called phase angle (FIG. 1).

A solid is in a state of a low release property, and a liquid is in a state of a high release property. From the concept of phase angle, an ideal solid refers to a perfectly elastic body, and its deformation is stored as energy. In other words, compared to elasticity (a recovery force to return to its original shape when an external force is applied), viscosity (a degree of content flowing when an external force is applied) is very low, and the phase angle is close to 0. Conversely, an ideal liquid refers to a perfectly viscous body, and its deformation is not stored as energy but lost. In other words, its elasticity is very low compared to its viscosity, and the phase angle approaches 90 degrees (FIG. 2).

The toothpaste composition of the present invention may have a phase angle of 20 to 90, specifically, 25 to 70, 30 to 50, or 30 to 40, and more specifically, 20 to 50, 20 to 40, or 20 to 30, but is not limited thereto. In particular, the toothpaste of the present invention is relatively close to a liquid state compared to conventional toothpastes. Due to this state, the toothpaste of the present invention has a very excellent release property. However, when the toothpaste is too close to the liquid state, it is difficult to discharge a desired amount of the toothpaste onto a toothbrush, and the shape retention property of the toothpaste when it is on a toothbrush becomes problematic. Therefore, it is preferable that the toothpaste have a predetermined level of phase angle.

As used herein, the term "viscosity" refers to a fluid's internal resistance. In the present invention, the viscosity represents viscosity of the toothpaste itself measured at room temperature, which is the result of measuring viscosity using a viscometer (Brookfield RVF) and a spindle bar of #7 at a rotational speed of 20 rpm.

As used herein, the term "low-shear viscosity" refers to shear viscosity measured at a low shear rate, which means how hard the state of a liquid in a solid is, and specifically means how well it withstands the state when an external force is applied. In the present invention, the low-shear viscosity is defined as viscosity at a shear rate of 0.1 $s^{-1}$. The low-shear viscosity may be easily measured using a rheometer.

The toothpaste composition may have a viscosity of 60,000 cP to 150,000 cP.

In a specific embodiment, the toothpaste composition of the present invention, which includes a peroxide, a thickener, and a spreading agent, may have a viscosity of 60,000 cP to 150,000 cP, specifically 70,000 cP to 150,000 cP, or more preferably 80,000 cP to 150,000 cP, and more specifically 90,000 cP to 150,000 cP even in an anhydrous base, but is not limited thereto. Depending on the viscosity, the toothpaste composition of the present invention has excellent sense of use, such as feelings of refreshment and cleaning, foam generation, flavor releasing power, etc.

In another specific embodiment, the toothpaste composition of the present invention, which includes silica and a chelating agent containing phosphate, may have a viscosity of 60,000 cP to 110,000 cP. Specifically, the toothpaste may exhibit the above viscosity by using carrageenan, xanthan gum, and thickening silica, but is not limited thereto. Owing to the above viscosity, dispersion of the abrasive and supersaturated phosphate may be stably achieved.

In still another specific embodiment, the toothpaste composition of the present invention, which includes a structurant and a thickener, may have a viscosity of 50,000 cP to 110,000 cP, specifically, 50,000 cP to 100,000 cP, even after being stored at 20° C. to 30° C. for 7 days, but is not limited thereto.

In the case of existing common toothpaste compositions, a toothpaste composition having a final viscosity of 40,000 cP or less, more specifically 20,000 cP or less was confirmed to have a very excellent release property, while a toothpaste composition having a viscosity of 50,000 cP or more was confirmed to have a very low release property. The toothpaste composition having a viscosity of 50,000 cP or more was confirmed to be suitable for a tube formulation as a paste formulation.

Unlike this toothpaste composition, the toothpaste composition of the present invention was confirmed to have a very excellent release property, even though its viscosity is 50,000 cP or more.

As used herein, the term "thickener" refers to a material that acts, as a binder in the toothpaste composition, to prevent the solid powder component from being separated from the liquid component. In addition to the function of preventing separation of toothpaste components, the thickener affects an appearance of the toothpaste, such as its shape retention property, transparency, etc., extrudability from a toothpaste tube, and properties when used, such as its release property during brushing, etc., and also affects efficacy and effects such as drug delivery, etc.

The thickener may be any type of polymer as long as it is a water-soluble polymer, and the thickener may consist of an organic thickener and an inorganic thickener.

The thickener of the present invention may be specifically one or more components selected from the group consisting of polyvinyl pyrrolidone (PVP), crosslinked PVP, polyvinyl alcohol (PVA), carboxymethyl cellulose (CMC), polyethylene glycol (PEG), carboxypolymethylene, carboxypropyl cellulose, poloxamer, carrageenan, carboxyvinyl polymers, xanthan gum, and polyvinyl pyrrolidone/vinyl acetate copolymers, and more specifically, it may be PVP or crosslinked PVP, but is not limited thereto.

The thickener of the toothpaste composition of the present invention may be an organic thickener or an inorganic thickener.

In the present invention, the "organic thickener" may specifically refer to a material that has a characteristic of a relatively high interaction with water, as compared with an interaction between organic thickeners. Due to this characteristic, the organic thickener may increase a thickening power of the toothpaste composition.

A content ratio of the structurant and the organic thickener of the present invention may be 0.2:1 to 6:1, specifically 0.3:1 to 5:1, and more specifically 0.5:1 to 4:1, but is not limited thereto.

The organic thickener of the present invention may be specifically one or more components selected from the group consisting of poloxamer, carbomer, polysaccharide, and carboxymethyl cellulose (CMC), and more specifically, one or more components selected from the group consisting of poloxamer, carbomer, and polysaccharide, but is not limited thereto.

The polysaccharide may be one or more components selected from the group consisting of xanthan gum, gellan gum, and locust bean gum, but is not limited thereto.

The inorganic thickener of the present invention may be one or more components selected from the group consisting of thickening silica, colloidal silica, and fumed silica, but is not limited thereto.

However, among the organic thickeners, carboxymethyl cellulose (CMC) is known to have side effects such as gastrointestinal disorders, constipation, diarrhea, etc., when excessively ingested. In this regard, the toothpaste composition according to an aspect of the present invention, which includes the structurant and the thickener, may not include carboxymethyl cellulose (CMC) in one exemplary embodiment, but is not limited thereto.

In particular, CMC has a characteristic that its hydration and dispersion do not occur well under conditions of low water content. Unlike the common toothpaste compositions with high water content, the toothpaste composition of the present invention with low water content is characterized by having a relatively high content of the inorganic thickener, instead of reducing the content of CMC.

In one exemplary embodiment of the present invention, the organic thickener may be included in an amount of 0.0001% to 2%, specifically 0.0001% to 1%, and more specifically 0.0001% to 0.6%, based on the total weight of the toothpaste composition, but is not limited thereto.

In the present invention, the inorganic thickener may be specifically one or more components selected from the group consisting of thickening silica, colloidal silica, and fumed silica, but is not limited thereto. The inorganic thickener is a component that does not greatly influence the release property, and exhibits sufficient viscosity even at low water content.

In one exemplary embodiment of the present invention, the inorganic thickener may be included in an amount of 1% to 30%, specifically 1.5% to 20%, and more specifically 2% to 10%, based on the total weight of the toothpaste composition, but is not limited thereto.

The toothpaste composition of the present invention may include water or no water.

This may vary depending on the composition of the toothpaste composition.

The toothpaste composition of the present invention may further include water in an amount of 15% by weight or less, 10% by weight or less, 1% by weight to 15% by weight, 1% by weight to 10% by weight, or 0.01% by weight to 10% by weight, specifically 1% by weight to 8% by weight, 1% by weight to 7% by weight, 0.01% by weight to 8% by weight, 0.01% by weight to 6% by weight, or 0.01% by weight to 5% by weight, and more specifically 2% by weight to 6% by weight, 0.01% by weight to 3% by weight, or 0.01% by weight to 2% by weight, based on the total weight of the toothpaste composition, but is not limited thereto.

In the case of not containing water or containing a small amount water, liquid polyols such as glycerin, PEG, PG, etc. may be included as a dispersion solvent of the toothpaste components, but are not limited thereto. Specifically, the liquid polyol may be included as a dispersion solvent of the toothpaste composition according to the present invention, as long as it does not cause a substantial increase in the viscosity of the composition by interaction with the thickener. In this case, the liquid polyol may be included in an amount of 20% to 80% based on the total weight of the composition, but is not limited thereto.

In particular, the liquid polyol may include glycerin, and in this regard, the glycerin may be included in an amount of 30% to 70%, specifically 40% to 70%, and more specifically 50% to 70%, based on the total weight of the composition, but is not limited thereto.

In general, when toothpaste compositions have high water content, the viscosity may be increased and the binding of the toothpaste base components may be strengthened due to the thickener, and as a result, the release property is weakened.

Accordingly, in order to maintain the shape retention property even when the water content is reduced, the present invention is characterized by including the structurant and the inorganic thickener, instead of reducing the content of the organic thickener, and thereby has excellent shape retention and release properties.

According to one exemplary embodiment of the present invention, it was confirmed that the toothpaste composition of the present invention has effects of improving the shape retention property and the release property.

As used herein, the term "shape retention property" refers to a property of maintaining the original shape of the toothpaste without it flowing down on a toothbrush when used by discharging the toothpaste on the toothbrush head. As the shape retention property is higher, a user's emotional satisfaction becomes higher.

However, when the thickening force is increased in order to improve the shape retention property, a bonding force between the components is created throughout the toothpaste due to the thickener, which may cause a problem in that a lump of toothpaste is not well released by saliva or tooth brushing.

Accordingly, the toothpaste composition of the present invention is characterized by having an excellent release property and an improved shape retention property at the same time.

As used herein, the term "release property" refers to dispersibility whereby a lump of toothpaste is released when it gets wet due to saliva or water after being discharged from a container containing the toothpaste to a toothbrush. Such excellent release property has a great influence on the rapid delivery of the medicinal ingredients supported in the toothpaste, foam generation, and consumers' sense of use.

As the toothpaste is more rapidly dispersed in water, it is more rapidly dispersed in the mouth, and this rapid dispersibility is an important factor in increasing the contact time of an anti-cavity ingredient with the tooth surface. In the present invention, it was confirmed that the rapid dispersibility is mainly related to the gel structure and thixotropy, and it was found that the thickening silica having a high oil absorption value has a great influence on the dispersibility. However, it was not easy to achieve excellent rheology while showing a viscosity of 50,000 cP or more only by thickening silica alone. Accordingly, it was confirmed that when the water content and the concentration of the thickener in the toothpaste are reduced, an excellent release property may be achieved even in the toothpaste composition having a viscosity suitable for being put in a tube as a paste formulation. In addition, it was confirmed that the sense of use and cleaning effect were also excellent due to the rapid release of flavor and active ingredients.

According to one exemplary embodiment of the present invention, it was confirmed that the toothpaste composition of the present invention has effects of improving a feeling of refreshment and flavor releasing power.

It was also confirmed that the toothpaste composition of the present invention has an excellent release property, and thereby has the excellent flavor releasing power and the improved feeling of refreshment.

According to one exemplary embodiment of the present invention, it was confirmed that the toothpaste composition of the present invention has effects of improving cleaning power and stain removal power.

It was also confirmed that the toothpaste composition of the present invention has an excellent release property, and thereby has excellent effects of removing stains on the tooth surface and brightening teeth.

The toothpaste composition of the present invention, which includes the structurant and the thickener, may further include one or more components selected from the group consisting of an abrasive, a surfactant, a humectant, a medicinal agent, an additive, and a foaming agent, but is not limited thereto.

As used herein, the term "abrasive" refers to a material that serves to remove dental plaque by polishing the surface of the tooth.

The abrasive of the present invention may be one or more selected from the group consisting of calcium pyrophosphate (CPP), calcium carbonate, insoluble sodium metaphosphate, zirconium silicate, hydroxyapatite, dental type silica, precipitated silica, hydrated alumina, silica gel, and dicalcium phosphate dehydrate (DCPD).

As used herein, the term "surfactant" refers to an agent that improves compatibility and cleansing effect of an oral composition and acts to quickly disperse and penetrate the medicinal ingredients to easily remove foreign substances in the mouth.

In the present invention, the surfactant may be an anionic surfactant and a non-ionic surfactant alone or in a mixture thereof. Preferably, the surfactant may be one or more selected from the group consisting of one or more anionic surfactants selected from the group consisting of sodium lauryl sulfate and sodium alkylsulfate; and one or more non-ionic surfactants selected from the group consisting of copolymers of polyoxyethylene and polyoxypropylene, polyoxyethylene sorbitan fatty acid, alkanolamide fatty acid ester, sucrose fatty acid ester, polyoxyethylene sorbitan fatty acid ester, polyoxyethylene fatty acid ester, polyoxyethylene castor oil derivatives, N-lauryl sarcosinate, sodium lauryl ether sulfate, polysorbate, decaglycerin monolaurate, sorbitan monooleate, alkyl polyglucoside, and cocoamide DEA.

As used herein, the term "humectant" refers to a substance that, as an essential base component for preparing ointment formulations, plays a role in preventing drying and solidification when the oral composition is exposed to air, providing gloss for the surface of the toothpaste, and also providing a sweetening effect during tooth brushing depending on the type.

In the present invention, the humectant may be one or more selected from the group consisting of a sorbitol solution, glycerin, polyethylene glycol, and propylene glycol.

As used herein, the term "medicinal agent" refers to a substance that may exhibit various medicinal effects for teeth cleansing and cleaning, and includes various functional ingredients and herbal materials that may be included in a toothpaste. Specifically, it may include a fluoride that forms a fluoride film on teeth and makes teeth resistant to an acid (lactic acid, etc.), which is a metabolite of caries bacteria.

As used herein, the term "foaming agent" refers to one that improves the sense of use of a product, helps the cleaning action, accelerates dispersion and penetration of other medicinal ingredients, and reduces the interfacial tension to easily remove foreign substances from the mouth.

As used herein, the term "additive" may refer to a flavoring agent, a sweetening agent, a pH adjusting agent, a brightening agent, an excipient, a preservative, and a coloring agent, and the content thereof is within the usual range.

The flavoring agent is edible, and synthetic flavoring agents (e.g., menthol, a green tea flavor, a mint flavor, etc.), extracts extracted from plants (e.g., peppermint oil, spearmint oil, sage oil, eucalyptol, eugenol, etc.), or extracts extracted from fruits may be used.

Sodium saccharin, xylitol, etc. may be most commonly used as the sweetening agent; sodium hydrogen carbonate, etc. may be used as the pH adjuster; and titanium oxide may be used as the brightening agent. In addition, hydroxyapatite may be used as the excipient, and food coloring is mainly used as the coloring agent.

The preservative is used to prevent microbial contamination that may occur during preparation and use of oral compositions and to help prolong the preservation of toothpastes. Sodium benzoate or parabens may be used as the preservative.

Still another aspect of the present invention provides a toothpaste composition including silica and a chelating agent containing phosphate, wherein the chelating agent is supersaturated to precipitate phosphate and the content of the precipitated phosphate is 2% or more, and specifically 2% to 10%, based on the total weight of the toothpaste composition.

The "precipitated phosphate" of the present invention refers to phosphate added to the composition in a maximum dissolution amount or more with respect to a solvent, particularly, water at 25° C., and when the solvent is water, the water content may be determined by a method of measuring water contents commonly known in the art, for example, the Karl Fischer method.

As used herein, the term "chelating agent" refers to a composition including a metal phosphate. Specifically, the chelating agent may be one or more components selected from the group consisting of tetrasodium pyrophosphate (TSPP), sodium acid pyrophosphate (SAPP), and sodium hexametaphosphate (SHMP), and more specifically may be SHMP, but is not limited thereto.

The chelating agent of the present invention is supersaturated to precipitate phosphate. The precipitated phosphate has particles, and due to these particles, the toothpaste composition of the present invention may realize a crunchy sensation of use, and may exhibit improved cleaning power and a whitening effect.

In the present invention, the particles of the precipitated phosphate serve as the abrasive, and enter between the teeth or between the teeth and the gums to physically remove the staining components, together with the force of brushing. Extrinsic staining materials in teeth have a mechanism in which the staining materials are slightly attached to the surface or the staining materials are attached to the tooth surface by metals, and therefore, they may be removed by brushing with a toothpaste containing a chelating agent and an abrasive, and the effect of cleaning the teeth may be obtained in a short period of time. In addition, if small particles are contained when brushing, they may impart a crunchy sensation of use while providing physical stimulation, and therefore, they may leave teeth feeling refreshed after tooth brushing, and may leave teeth feeling cleaner. Most preferably, the particles have a size and strength that may impart a crunchy sensation during tooth brushing.

As used herein, the term "maximum dissolution amount" of phosphate refers to the amount of phosphate that may be dissolved to the maximum until immediately before the supersaturation state of phosphate, depending on the content of used water.

As used herein, the term "excess amount" of phosphate refers to the amount of phosphate that is precipitated to form particles when phosphate is added in the maximum dissolution amount or more.

The amount of the supersaturated and precipitated phosphate of the present invention may be 2% or more, specifically 2% to 10%, more specifically 3% to 10% or 4% to 9%, and more specifically 5% to 8% or 5.5% to 7.5%, based on the total weight of the toothpaste composition, but is not limited thereto.

In particular, when the amount of the supersaturated and precipitated phosphate is 2% or more based on the total weight of the toothpaste composition, the crunchy sensation due to particles is realized, and the cleaning power, stain removal power, and whitening effect become excellent. However, when the amount of the supersaturated and precipitated phosphate exceeds 10% based on the total weight of the toothpaste composition, it may cause irritation in the mouth.

In the present invention, the solubility of phosphate may be 6 g/100 mL to 100 g/100 mL at 25° C., specifically 20 g/100 mL at 25° C., but is not limited thereto. The solubility of TSPP is 6.7 g/100 mL (25° C.), the solubility of SAPP is 12.5 g/100 mL (25° C.), and the solubility of SHMP is 50 g/100 mL (25° C.).

In particular, when the solubility in water is too low, precipitation in the toothpaste occurs during storage, which is not beneficial to the stability of the composition. In the case of tetrapotassium pyrophosphate (TKPP) (187 g/100 mL (25° C.)) and potassium acid pyrophosphate (KAPP) (149.25 g/100 mL (25° C.)), the solubility of which is 100 g/100 mL or more, when 10% phosphate with respect to 10% water is used, it is mostly dissolved, which is not suitable. Pyrophosphate or metaphosphate has an excellent chelating effect to help the cleaning power. However, when pyrophosphate or metaphosphate is used in an amount of 10% or more, it may cause irritation in teeth, which is not suitable.

In the present invention, the average diameter of the supersaturated and precipitated phosphate particles may be 75 µm to 180 µm, specifically 105 µm to 180 µm, and more specifically 105 µm to 150 µm, but is not limited thereto. In particular, when the diameter of the supersaturated and precipitated phosphate particles is less than 75 µm, it is difficult to feel the crunchy sensation when the toothpaste composition is used. When the diameter is 75 µm or more, the most excellent crunchy sensation and the excellent cleaning power are achieved.

In the present invention, the silica refers to silicon dioxide, and the silica used in the toothpaste agent is prepared by using amorphous silicon dioxide as a main component. Silica has different properties and abrasiveness depending on a processing method, and may be classified into abrasive silica and thickening silica according to the size of particles.

The silica of the present invention may be used in an amount of 15% to 50%, specifically 20% to 40%, and more specifically 20% to 30%, based on the total weight of the toothpaste composition, but is not limited thereto.

The silica of the present invention may include abrasive silica, and the abrasive silica may be used in an amount of 50% to 90%, specifically 60% to 90%, and more specifically 70% to 90%, based on the total weight of the silica, but is not limited thereto.

The toothpaste composition of the present invention, which includes the silica and the chelating agent containing phosphate, may include water, and the content of water is the same as described above.

In the present invention, phosphate may be supersaturated and precipitated by reducing the content of water. However, considering the solubility of phosphate, the content of water may be appropriately adjusted.

The toothpaste composition of the present invention, which includes the silica and the chelating agent containing phosphate, may be used for whitening and stain removal. According to one exemplary embodiment of the present invention, the toothpaste composition of the present invention was confirmed to have the effects of improving the cleaning power and the stain removal power. The toothpaste composition of the present invention was confirmed to have the excellent effect of removing stains on the tooth surface and brightening teeth.

According to one exemplary embodiment of the present invention, it was confirmed that the toothpaste composition of the present invention realized the crunchy sensation to improve sense of use.

The toothpaste composition of the present invention, which includes the silica and the chelating agent containing phosphate, may further include one or more components selected from the group consisting of an abrasive, a surfactant, a humectant, a medicinal agent, an additive, and a foaming agent, but is not limited thereto.

In particular, the abrasive, the surfactant, the humectant, the medicinal agent, the additive, and the foaming agent are the same as described above.

According to still another aspect of the present invention, the toothpaste composition of the present invention includes a peroxide, a thickener, and a spreading agent.

Even when the toothpaste composition of the present invention, which includes the peroxide, the thickener, and the spreading agent, is contained in a toothpaste container made of a hydrophobic material such as PE, phase stability of the toothpaste composition may be maintained.

The toothpaste composition of the present invention provides a toothpaste composition in which the peroxide and the thickener are separated from each other.

Particularly, even when the peroxide and the thickener are separated from each other in the toothpaste composition, phase stability of the toothpaste composition may be maintained, and thus activity of the hydrogen peroxide is not deteriorated, and a release rate of the hydrogen peroxide is remarkably high as compared with common toothpaste compositions including a complex of PVP and hydrogen peroxide, thereby achieving a more excellent whitening effect.

As used herein, the term "spreading agent" refers to a material that imparts hydrophobicity to the toothpaste composition to solve the problem of separation from polyethylene (PE) in the toothpaste tube and phase separation, thereby improving the phase stability of the toothpaste composition, and the spreading agent is a safe material for the human body. The toothpaste composition of the present invention using the spreading agent tightly sticks to the material of the toothpaste tube, so that water generated by hydrolysis does not exist between the toothpaste and the tube, thereby suppressing phase separation, and as a result, stability of the toothpaste is remarkably improved.

The spreading agent of the present invention may be one or more components selected from the group consisting of Span 20 (sorbitan monolaurate), Span 40 (sorbitan monopalmitate), Span 60 (sorbitan monostearate), Span 80 (sorbitan monooleate), Span 85 (sorbitan trioleate), and TWEEN (POE sorbitan fatty acid ester), and specifically may be Span 80 (sorbitan monooleate), Span 60 (sorbitan monostearate), or a combination thereof, but is not limited thereto.

The content of the spreading agent of the present invention may be 0.1% by weight to 10% by weight, specifically 0.2% by weight to 5% by weight, and more specifically 0.2% by weight to 2.5% by weight, based on the total weight of the toothpaste composition, but is not limited thereto.

As used herein, the term "thickener" is the same as described above.

In the toothpaste composition of the present invention, which includes the peroxide, the thickener, and the spreading agent, the thickener has excellent compatibility with hydrogen peroxide and has a swelling effect, and thus exhibits the excellent thickening effect even under anhydrous conditions, and exhibits excellent sense of use due to no stickiness.

When the thickener of the present invention forms a complex with hydrogen peroxide, it is known to prevent degradation of hydrogen peroxide by physically separating hydrogen peroxide blended in the toothpaste composition from other components blended in the toothpaste such as water, the abrasive, the foaming agent, and the active ingredient of toothpaste, thereby preventing a problem of lowered titer of hydrogen peroxide during distribution of the toothpaste composition. However, since this complex form of thickener—hydrogen peroxide acts as a hindrance factor in exerting the activity of hydrogen peroxide at the time when a consumer actually uses the toothpaste, it is necessary to pretreat or post-treat with a composition containing a separate hydrogen peroxide decomposition agent.

The content of the thickener of the present invention may be 5% by weight to 20% by weight, specifically 7% by weight to 17% by weight, and more specifically 10% by weight to 15% by weight, based on the total weight of the toothpaste composition, but is not limited thereto.

The peroxide of the present invention has a tooth whitening effect because oxygen generated during peroxide decomposition bleaches staining materials on teeth. Since the peroxide has a relatively low molecular weight, it is effective in achieving high tooth-whitening power at the same weight.

The peroxide of the present invention may be specifically one or more components selected from the group consisting of hydrogen peroxide, carbamide peroxide, calcium peroxide, sodium percarbonate, sodium perborate, and tetrasodium pyrophosphate peroxidate, and more specifically, the peroxide may be hydrogen peroxide, but is not limited thereto.

The content of the peroxide of the present invention may be 0.1% by weight to 10% by weight, specifically 0.5% by weight to 5% by weight, and more specifically 3% by weight, based on the total weight of the toothpaste composition, but is not limited thereto.

The toothpaste composition of the present invention may further include an abrasive.

The abrasive is the same as described above.

In one specific embodiment, the toothpaste composition of the present invention, which includes the peroxide, the thickener, and the spreading agent, may include one or more abrasives selected from the group consisting of calcium pyrophosphate (CPP), insoluble sodium metaphosphate, zirconium silicate, and hydroxyapatite, and specifically, the tooth composition may be CPP in terms of stably maintaining activity of peroxide in the toothpaste composition, but is not limited thereto.

Since the peroxide and the abrasive show poor compatibility with each other, the peroxide and the abrasive are not used together in the toothpaste composition. However, the toothpaste composition of the present invention may include both the peroxide and the abrasive, and therefore, a synergistic effect may be obtained to achieve an excellent whitening effect.

The content of the abrasive of the present invention may be 5% by weight to 20% by weight, specifically 7% by weight to 17% by weight, and more specifically 10% by weight to 15% by weight, based on the total weight of the toothpaste composition, but is not limited thereto.

In one specific embodiment, the toothpaste composition of the present invention, which includes the peroxide, the thickener, and the spreading agent, may include no water, but is not limited thereto.

The toothpaste composition of the present invention may be used for tooth whitening.

Specifically, the toothpaste composition of the present invention, which includes the peroxide, the thickener, and the spreading agent, and in which the peroxide and the thickener are separated from each other, may exhibit a much more excellent tooth whitening effect due to remarkably rapid decomposition of hydrogen peroxide when actually used, as compared with common toothpaste compositions including the thickener and hydrogen peroxide in the complex form.

The toothpaste composition of the present invention may have improved phase stability even at 30° C. to 60° C., and specifically, no phase separation phenomenon of the peroxide occurs even after 4 weeks. The toothpaste composition tightly sticks to the tube, so that water generated by hydrolysis does not exist, thereby suppressing the phase separation phenomenon. Therefore, even in the toothpaste composition of the present invention, which includes the peroxide, the thickener, and the spreading agent, and in which the peroxide and the thickener are separated from each other, stability of the toothpaste may be remarkably improved.

The toothpaste composition of the present invention, which includes the peroxide, the thickener, and the spreading agent, may further include one or more components selected from the group consisting of a surfactant, a humectant, a medicinal agent, an additive, and a foaming agent, but is not limited thereto.

The abrasive, the surfactant, the humectant, the medicinal agent, the additive, and the foaming agent are the same as described above.

[Mode for Carrying Out the Invention]

Hereinafter, the present invention will be described in more detail with reference to the following Examples. However, the following Examples are for illustrative purposes only, and the scope of the present invention is not intended to be limited by these Examples.

EXAMPLES 1 TO 4 AND COMPARATIVE EXAMPLES 1 TO 4

Toothpaste compositions of Examples 1 to 4 and Comparative Examples 1 to 4 were prepared according to components and composition ratios shown in Table 1 below.

Specifically, a structurant (carrageenan or carbomer) and a thickener (poloxamer or xanthan gum) were dispersed in a humectant (PEG, glycerin, etc.) in advance, and salt components (sodium fluoride, saccharin, etc.) dissolved or dispersed in purified water were added thereto, followed by hydration under stirring. Silica (abrasive silica or thickening silica) was mixed therewith by dispersion, followed by stirring for 20 minutes. Thereafter, a foaming agent (SLS, etc.) was added thereto, followed by stirring under vacuum for 20 minutes. A flavor was added thereto, followed by stirring under vacuum for 20 minutes, and thereby each toothpaste composition was prepared. However, the toothpaste compositions of the present invention are not limited to the above preparation method.

TABLE 1

| | Example 1 | Example 2 | Example 3 | Example 4 | Comparative Example 1 | Comparative Example 2 | Comparative Example 3 | Comparative Example 4 |
|---|---|---|---|---|---|---|---|---|
| Glycerin | 56.05 | 54.95 | 58.55 | 54.2 | 38.75 | 45.15 | 54.55 | 45.55 |
| Abrasive silica | 20 | 15 | 15 | 20 | 5 | 15 | 25 | 22 |
| Thickening silica | 2 | 10 | 7 | 5 | 9 | 0 | 0 | 0 |
| STPP (sodium tripolyphosphate) | 4 | 4 | | | 8 | 4 | 4 | |
| SHMP (sodium hexametaphosphate) | | | | 8 | | | | |

TABLE 1-continued

|  | Example 1 | Example 2 | Example 3 | Example 4 | Comparative Example 1 | Comparative Example 2 | Comparative Example 3 | Comparative Example 4 |
|---|---|---|---|---|---|---|---|---|
| TSPP (tetrasodium pyrophosphate) |  |  | 4 |  |  |  |  | 4 |
| Purified water | 10 | 8 | 7 | 5 | 30 | 27 | 8 | 20 |
| PEG | 3 | 3 | 3 | 3 | 3 | 3 | 3 | 3 |
| Flavor | 1.0 | 1.0 | 1.0 | 1.0 | 1.0 | 1.0 | 1.0 | 1.0 |
| Triphosphate | 1.0 | 1.0 | 1.0 | 1.0 | 1.0 | 1.0 | 1.0 | 1.0 |
| SLS (sodium lauryl sulfate) | 2.0 | 2.0 | 2.0 | 2.0 | 2.0 | 2.0 | 2.0 | 2.0 |
| Carrageenan | 0.4 | 0.2 |  | 0.15 |  |  | 0.2 |  |
| Carbomer |  |  | 0.5 |  |  |  |  | 0.5 |
| Poloxamer |  | 0.4 |  |  |  |  | 0.4 |  |
| CMC |  |  |  |  | 1.5 | 0.45 |  |  |
| Xanthan gum | 0.1 |  | 0.5 | 0.3 | 0.1 | 0.75 | 0.4 | 0.5 |
| Saccharin |  |  |  | 0.15 | 0.2 | 0.2 |  |  |
| Titanium oxide | 0.23 | 0.23 | 0.23 | 0.23 | 0.23 | 0.23 | 0.23 | 0.23 |
| Sodium fluoride | 0.22 | 0.22 | 0.22 | 0.22 | 0.22 | 0.22 | 0.22 | 0.22 |

Experimental Example 1. Measurement of Physical Properties of Toothpastes (1) Method of Measuring Viscosity Viscosity was measured using a viscometer (Brookfield RVF) and a spindle bar of #7 at a rotational speed of 20 rpm (Spindle bar) at 25° C.

(2) Method of Measuring Suitability for Tube

It was evaluated whether each of the toothpaste compositions could be injected into a common toothpaste tube.

(3) Method of Measuring Release Property

1) Method of Measuring Consumers' Evaluation of Release Property

Slurries were directly prepared and stirred for a predetermined time, and then consumers directly evaluated the degree of the release property. 12 adults were allowed to brush their teeth using each of the toothpastes of Examples 1 to 4 and Comparative Examples 1 to 4 in a length of 1 cm, and to evaluate the release property with a 5-point scale: 5 points given for very good, 4 points for good, 3 points for moderate, 2 points for slightly poor, and 1 point for very poor.

2) Method of measuring release property using laboratory beakers 12.5 g of each toothpaste was put in a 50 mL beaker, and 20 g of water was added thereto, followed by vigorous stirring for 30 seconds using a glass rod. The toothpaste slurry in the beaker was transferred to a stainless plate, and then the remaining amount and shape thereof were visually examined, and rated as follows: 5 points given for nothing left after being completely dissolved, 4 points for a small amount left but mostly dissolved, 3 points for no large lumps left after being fairly dissolved, 2 points for a considerable amount of undissolved lumps, and 1 point for large lumps not dissolved but clumped together.

(4) Method of Measuring Phase Angle

Phase angle (δ) was measured by measuring G"/G', a loss tangent (tan δ) value, with respect to the toothpaste compositions of Examples 1 to 4 and Comparative Examples 1 to 4 using a rheometer.

(5) Method of Measuring Low-Shear Viscosity

Shear viscosity was measured with respect to the toothpaste compositions of Examples 1 to 4 and Comparative Examples 1 to 4 at a shear rate of $0.1\ s^{-1}$.

(6) Results of Measuring Physical Properties

The results of measuring the viscosity, release property (consumers' evaluation, laboratory evaluation), phase angle, and low-shear viscosity with respect to the toothpaste compositions of Examples 1 to 4 and Comparative Examples 1 to 4 are shown in Table 2 below.

TABLE 2

|  | Example 1 | Example 2 | Example 3 | Example 4 | Comparative Example 1 | Comparative Example 2 | Comparative Example 3 | Comparative Example 4 |
|---|---|---|---|---|---|---|---|---|
| Viscosity | 70,000 | 80,000 | 50,000 | 100,000 | 110,000 | 20,000 | 40,000 | 25,000 |
| Tube suitability | Pass | Pass | Pass | Pass | Pass | Fail | Fail | Fail |
| Releasing property (consumers' evaluation scale) | 5 | 4 | 4 | 5 | 2.5 | 4 | 4 | 3 |
| Releasing property (laboratory evaluation) | 4 | 4 | 4 | 5 | 1 | 4 | 4 | 2 |
| Phase angle | 32 | 35 | 37 | 30 | 11.1 | 27.4 | 35 | 8.2 |
| Low-shear viscosity (cP) | 858,000 | 566,000 | 388,000 | 797,000 | 8,135,000 | 413,000 | 699,000 | 1,530,000 |

From the results of Table 2, it was confirmed that all toothpaste compositions of Examples 1 to 4 according to the present invention were given very excellent ratings with regard to the release property (consumers' evaluation and laboratory evaluation) even at a viscosity of 50,000 or more, as compared with the toothpaste compositions of Comparative Examples 1 to 4, and showed excellent suitability for toothpaste tubes and phase angle of 25 or more.

Experimental Example 2. Measurement of Sense of Use (1) Method of Measuring Feeling of Refreshment and Flavor Releasing Power 12 adults were allowed to brush their teeth using the same toothbrush (Reach Sensitive Toothbrush) and each of the toothpaste compositions of Examples 1 to 4 and Comparative Examples 1 to 4 in a length of 1 cm for 1 minute, and then the flavor releasing power and the feeling of cleaning were surveyed.

Survey Response Criteria

5: A feeling of refreshment and a flavor releasing power are obviously better than those of toothpastes used before.

4: A feeling of refreshment and a flavor releasing power are slightly better than those of toothpastes used before.

3: A feeling of refreshment and a flavor releasing power are similar to those of toothpastes used before.

2: A feeling of refreshment and a flavor releasing power are slightly worse than those of toothpastes used before.

1: A feeling of refreshment and a flavor releasing power are obviously worse than those of toothpastes used before.

(2) Method of Measuring Stain Removal Effect/Cleaning Effect 20 adult males who are daily smokers were allowed to brush their teeth using the same toothbrush (Reach Sensitive Toothbrush) and each of the toothpaste compositions of Examples 1 to 4 and Comparative Examples 1 to 4 in a length of 1 cm for 1 minute three times a day for 4 weeks, and then the cleaning power was surveyed.

Survey Response Criteria

5: You feel like stains on the tooth surface are removed and the teeth are brightened.

4: You feel like stains on the tooth surface are slightly removed.

3: You feel like the teeth are slightly brightened.

2: You feel like the tooth surface becomes smooth.

1: You feel like there is no great difference before and after use.

(3) Results of Measuring Sense of Use

The results of measuring the feeling of refreshment, flavor releasing power, and stain removal effect/cleaning effect with respect to the toothpaste compositions of Examples 1 to 4 and Comparative Examples 1 to 4 are shown in Table 3 below.

TABLE 3

|  | Example 1 | Example 2 | Example 3 | Example 4 | Comparative Example 1 | Comparative Example 2 | Comparative Example 3 | Comparative Example 4 |
| --- | --- | --- | --- | --- | --- | --- | --- | --- |
| Feeling of Refreshment, Flavor releasing power | 4 | 5 | 5 | 5 | 3 | 4 | 2 | 1 |
| Stain removal, Cleaning effect | 4 | 5 | 4 | 5 | 3 | 3 | 3 | 3 |

From the results of Table 3, it was confirmed that, as compared with the toothpaste compositions of Comparative Examples 1 to 4, all toothpaste compositions of Examples 1 to 4 according to the present invention obviously showed a more excellent feeling of refreshment and flavor releasing power than toothpastes used before, and showed an excellent stain removal effect and cleaning effect, as it was evaluated that the stains on the tooth surface seemed to be removed and the teeth seemed to be brightened.

Preparation of Examples 5 to 9 and Comparative Examples 5 to 9

Toothpaste compositions of Examples 5 to 9 and Comparative Examples 5 to 9 were prepared according to components and composition ratios shown in Table 4 below. Specifically, other components (additive, etc.) dissolved in purified water were mixed with a thickener (carrageenan or xanthan gum) that had been dispersed in a humectant (PEG or glycerin), and then silica (abrasive or thickening silica) was added thereto, followed by stirring for about 20 minutes. A surfactant (SLS, etc.) was added thereto, followed by stirring under vacuum for about 20 minutes. A chelating agent (SHMP, TSPP, or SAPP) and a flavor were added thereto, followed by stirring under vacuum for about 20 minutes, and thereby each toothpaste was prepared.

The viscosity of each toothpaste composition was measured using a viscometer (Brookfield RVF) and a spindle bar of #7 at a rotational speed of 20 rpm at 25° C. for 5 rotations (15 seconds), and the results are shown in Table 4 below.

TABLE 4

| | Example 5 | Example 6 | Example 7 | Example 8 | Example 9 | Comparative Example 5 | Comparative Example 6 | Comparative Example 7 | Comparative Example 8 | Comparative Example 9 |
|---|---|---|---|---|---|---|---|---|---|---|
| Water | 2.72 | 4.00 | 5.00 | 5.00 | 5.00 | 16.95 | 18.95 | 12.00 | 13.00 | 16.00 |
| Microbeads | | | | | | 2.00 | | | | |
| TSPP | 5.68 | | | | | | | | | |
| SAPP | | 6.00 | | | | | | | | |
| >75 μm SHMP | | | 8.00 | | | | | 8.00 | 8.00 | 8.00 |
| 105-180 μm SHMP | | | | 8.00 | 10.00 | | | | | |
| Sodium phosphate tribasic | 1.00 | 1.00 | 1.00 | 1.00 | 1.00 | 1.00 | 1.00 | 1.00 | 1.00 | 1.00 |
| Abrasive silica | 20.00 | 20.00 | 20.00 | 20.00 | 20.00 | 20.00 | 20.00 | 20.00 | 20.00 | 20.00 |
| Thickening silica | 5.00 | 5.00 | 5.00 | 5.00 | 5.00 | 9.00 | 9.00 | 3.00 | 3.00 | 5.00 |
| Glycerin | 58.60 | 57.00 | 54.00 | 54.00 | 52.00 | 43.00 | 43.00 | 48.15 | 47.15 | 41.95 |
| PEG (polyethylene glycol) | 3.00 | 3.00 | 3.00 | 3.00 | 3.00 | 3.00 | 3.00 | 3.00 | 3.00 | 3.00 |
| Carrageenan | 0.15 | 0.15 | 0.15 | 0.15 | 0.15 | 1.20 | 1.20 | 0.80 | 0.80 | 1.20 |
| Xanthan gum | 0.30 | 0.30 | 0.30 | 0.30 | 0.30 | 0.30 | 0.30 | 0.50 | 0.50 | 0.30 |
| SLS (sodium lauryl sulfate) | 2.00 | 2.00 | 2.00 | 2.00 | 2.00 | 2.00 | 2.00 | 2.00 | 2.00 | 2.00 |
| Titanium oxide | 0.23 | 0.23 | 0.23 | 0.23 | 0.23 | 0.23 | 0.23 | 0.23 | 0.23 | 0.23 |
| Sodium saccharin | 0.10 | 0.10 | 0.10 | 0.10 | 0.10 | 0.10 | 0.10 | 0.10 | 0.10 | 0.10 |
| Flavor | 1.00 | 1.00 | 1.00 | 1.00 | 1.00 | 1.00 | 1.00 | 1.00 | 1.00 | 1.00 |
| Sodium fluoride | 0.22 | 0.22 | 0.22 | 0.22 | 0.22 | 0.22 | 0.22 | 0.22 | 0.22 | 0.22 |
| Maximum dissolution amount | 0.18 | 0.50 | 2.50 | 2.50 | 2.50 | — | — | 6.00 | 6.50 | 8.00 |
| Supersaturation (excess amount) | 5.50 | 5.50 | 5.50 | 5.50 | 7.50 | — | — | 2.00 | 1.50 | 0.00 |
| Viscosity (cP) | 85,000 | 80,000 | 75,000 | 76,000 | 78,000 | 85,000 | 80,000 | 76,000 | 74,000 | 85,000 |

Experimental Example 3. Measurement of In Vitro Cleaning Effect and Whitening Effect (1) Method of Measuring In Vitro Cleaning Effect and Whitening Effect Artificial teeth (tooth enamel, hydroxyapatite, which is a material primarily constituting dentin) were prepared into tablet specimens, and stained using tooth staining materials such as tea, coffee, mucin, metal salts, etc. Thereafter, the hydroxyapatite tablet specimens were fixed using a brushing machine for testing cleaning power. The toothpaste composition of the present invention was brushed in a slurry state at the actual concentration (25 g/40 mL) 5400 times at a speed of 90 times per second, and the degree of brightness of the stained artificial tooth specimen before and after cleaning was determined by measuring a color change (ΔE) in the surface of hydroxyapatite tablet specimen using a chromameter.

(2) Results of Measuring In Vitro Cleaning Effect and Whitening Effect

The results of measuring an in vitro tooth whitening effect with respect to the toothpaste compositions of Examples 5 to 9 and Comparative Examples 5 to 9 are shown in Table 5 below.

TABLE 5

| | Example 5 | Example 6 | Example 7 | Example 8 | Example 9 | Comparative Example 5 | Comparative Example 6 | Comparative Example 7 | Comparative Example 8 | Comparative Example 9 |
|---|---|---|---|---|---|---|---|---|---|---|
| ΔE | 16.1 | 16.7 | 18.5 | 20.1 | 22.5 | 9.0 | 8.0 | 14.6 | 14.5 | 14.0 |

From the results of Table 5, it was confirmed that the toothpaste compositions of Examples 7 to 9 using SHMP as phosphate showed a whitening effect 2.1 to 2.8 times higher than that of the toothpaste compositions of Comparative Examples 5 and 6 without SHMP as phosphate, and also showed a whitening effect 1.3 to 1.6 times higher than that of the toothpaste compositions of Comparative Examples 7 to 9 using SHMP as phosphate and water in an amount of 10% or more, based on the total weight of the toothpaste composition.

In addition, it was confirmed that the toothpaste compositions of Example 5 and 6 each using TSPP or SAPP as phosphate showed a whitening effect 1.8 to 2.1 times higher than that of the toothpaste compositions of Comparative Examples 5 and 6 using no SHMP as phosphate.

These results suggest that the toothpaste compositions having more than 2% of phosphate supersaturation based on the total weight of the toothpaste composition, by including SHMP and 10% or less of water based on the total weight of the toothpaste composition, provide a feeling of particles to effectively remove staining materials on the tooth surface, thereby exhibiting a more excellent tooth whitening effect.

Experimental Example 4. Measurement of Sense of Use (1) Method of Measuring Crunchy Sensation 12 adults were allowed to brush their teeth using the same toothbrush (Reach Sensitive Toothbrush) and each of the toothpaste compositions of Examples 5 to 9 and Comparative Examples 5 to 9 in a length of 1 cm for 1 minute three times a day for 2 weeks, and then the crunchy sensation was surveyed.

Survey Response Criteria

5: You feel like a crunchy sensation is obviously better than that of toothpastes used before.

4: You feel like a crunchy sensation is slightly better than that of toothpastes used before.

3: You feel particles in the toothpaste.

2: You feel like a crunchy sensation is similar to that of toothpastes used before.

1: You feel like a crunchy sensation is obviously worse than that of toothpastes used before.

(2) Method of Measuring Feeling of Cleaning 12 adults were allowed to brush their teeth using the same toothbrush (Reach Sensitive Toothbrush) and each of the toothpaste compositions of Examples 5 to 9 and Comparative Examples 5 to 9 in a length of 1 cm for 1 minute three times a day for 2 weeks, and then the feeling of cleaning was surveyed.

Survey Response Criteria

5: After brushing teeth, you feel the tooth surface is clean and feel a squeaky sound.

4: After brushing teeth, you feel the tooth surface is clean.

3: After brushing teeth, you feel a squeaky sound.

2: You feel like there is no great difference in cleaning power compared to toothpastes used before.

1: You feel like the cleaning power is worse than that of toothpastes used before.

(3) Results of Measuring Sense of Use

The results of measuring the crunchy sensation and the feeling of cleaning with respect to the toothpaste compositions of Examples 5 to 9 and Comparative Examples 5 to 9 are shown in Table 6 below.

TABLE 6

|  | Example 5 | Example 6 | Example 7 | Example 8 | Example 9 | Comparative Example 5 | Comparative Example 6 | Comparative Example 7 | Comparative Example 8 | Comparative Example 9 |
|---|---|---|---|---|---|---|---|---|---|---|
| Crunchy sensation | 3.5 | 3.5 | 4 | 4.5 | 5 | 3 | 2 | 2.5 | 2.5 | 2 |
| Feeling of cleaning | 4 | 4 | 4 | 4.5 | 5 | 2 | 2 | 3 | 3 | 3 |

From the results of Table 6, it was confirmed that, as compared with the toothpaste compositions of Comparative Examples 5 to 9, all toothpaste compositions of Example 5 to 9 according to the present invention showed a much more excellent crunchy sensation than toothpastes used before, and showed the excellent feeling of cleaning, as it was evaluated that the tooth surface seemed to be clean and a squeaky sound could be felt.

Preparation of Examples 10 to 17

Toothpaste compositions of Examples 10 to 17 were prepared according to components and composition ratios shown in Table 7 below.

Specifically, all liquid components were added to a humectant (PG, PEG, glycerin), followed by mixing well. Then, an abrasive (CPP, silica) and a thickener (PVP or crossed linked PVP) were well dispersed. Other components (additive, etc.) were dispersed therein, followed by stirring for about 20 minutes. A surfactant (SLS, etc.) was added thereto, followed by stirring under vacuum for about 20 minutes. Hydrogen peroxide and a flavor were added thereto, followed by stirring under vacuum for about 20 minutes, and thereby each toothpaste was prepared. The preparation method of the present invention is not limited thereto.

TABLE 7

| | Example 10 | Example 11 | Example 12 | Example 13 | Example 14 | Example 15 | Example 16 | Example 17 |
|---|---|---|---|---|---|---|---|---|
| PG | 32.3 | 33.3 | 32.8 | 41.88 | 42.88 | 42.38 | 34.8 | 34.8 |
| PEG | 10 | 10 | 10 | 10.2 | 10.2 | 10.2 | 10 | 10 |
| Glycerin | 10 | 10 | 10 | 2.5 | 2.5 | 2.5 | 10 | 10 |
| EO-PO block copolymer | 10 | 10 | 10 | 11.4 | 11.4 | 11.4 | 10 | 10 |
| NaF | 0 | 0 | 0 | 0.21 | 0.21 | 0.21 | 0 | 0 |
| SMFP | 0.68 | 0.68 | 0.68 | | | | 0.68 | 0.68 |
| TSPP | 1.5 | 1.5 | 1.5 | 1.0 | 1.0 | 1.0 | 1.5 | 1.5 |
| SAPP | 0.5 | 0.5 | 0.5 | 1.0 | 1.0 | 1.0 | 0.5 | 0.5 |
| Silica | 2 | 2 | 2 | 3.0 | 3.0 | 3.0 | 2 | 2 |
| CPP | 15 | 15 | 15 | 10 | 10 | 10 | 15 | 15 |
| Sorbitan monooleate | 2 | 0 | 0.5 | 2 | 0 | 0.5 | 2 | 2 |
| Sorbitan monostearate | 0 | 1 | 0 | 0 | 1 | 0 | 0 | 0 |
| Polysorbate 80 | 0 | 0 | 1.0 | 0 | 0 | 1.0 | 0 | 0 |
| PVP | 0 | 0 | | | | | 0 | 5.5 |
| Crosslinked PVP | 10.5 | 10.5 | 10.5 | 11.0 | 11.0 | 11.0 | 5.5 | 0 |
| PVP-$H_2O_2$ complex ($H_2O_2$ 19%) | 0 | 0 | 0 | 0 | 0 | 0 | 0 | 5.5 |
| Crosslinked PVP-$H_2O_2$ complex ($H_2O_2$ 19%) | 0 | 0 | 0 | 0 | 0 | 0 | 5.5 | 0 |
| $H_2O_2$ (35%) | 3.0 | 3.0 | 3.0 | 3.0 | 3.0 | 3.0 | 0 | 0 |
| SLS | 2.0 | 2.0 | 2.0 | 2 | 2 | 2 | 2 | 2.0 |
| Sodium saccharin | 0.5 | 0.5 | 0.5 | 0.8 | 0.8 | 0.8 | 0.5 | 0.5 |
| Sucralose | 0.02 | 0.02 | 0.02 | 0.01 | 0.01 | 0.01 | 0.02 | 0.02 |
| Water | 0 | 0 | 0 | 0 | 0 | 0 | 0 | 0 |

Preparation of Comparative Examples 10 to 15

Toothpaste compositions of Comparative Examples 10 to 14 were prepared according to components and composition ratios shown in Table 8 below in the same manner as in Examples 10 to 17, except for whether hydrogen peroxide was used or not, whether CPP (calcium pyrophosphate) was used or not, and that a thickener (crosslinked PVP-$H_2O_2$ complex) and a spreading agent were not used. A commercially available MEDIAN dental whitening toothpaste (containing hydrogen peroxide, containing no abrasive, and containing water) was used as Comparative Example 15.

TABLE 8

| | Comparative Example 10 | Comparative Example 11 | Comparative Example 12 | Comparative Example 13 | Comparative Example 14 |
|---|---|---|---|---|---|
| PG | 34.3 | 36.81 | 34.31 | 51.81 | 37.3 |
| PEG | 10 | 10 | 10 | 10 | 10 |
| Glycerin | 10 | 10 | 10 | 10 | 10 |
| EO-PO block copolymer | 10 | 10 | 10 | 10 | 10 |
| NaF | 0 | 0 | 0 | 0 | 0 |
| SMFP | 0.68 | 0.68 | 0.68 | 0.68 | 0.68 |
| TSPP | 1.5 | 1.5 | 1.5 | 1.5 | 1.5 |
| SAPP | 0.5 | 0.5 | 0.5 | 0.5 | 0.5 |
| Silica | 2 | 2 | 2 | 2 | 2 |
| CPP | 15 | 15 | 15 | 0 | 15 |
| Sorbitan monooleate | 0 | 0 | 0 | 0 | 0 |
| Sorbitan mono stearate | 0 | 0 | 0 | 0 | 0 |
| Polysorbate 80 | 0 | 0 | 0 | 0 | 0 |
| PVP | 0 | 0 | 10.5 | 0 | 0 |
| Crosslinked PVP | 10.5 | 5.5 | 0 | 5.5 | 10.5 |
| PVP-$H_2O_2$ complex | 0 | 0 | 0 | 0 | 0 |

TABLE 8-continued

|  | Comparative Example 10 | Comparative Example 11 | Comparative Example 12 | Comparative Example 13 | Comparative Example 14 |
|---|---|---|---|---|---|
| Crosslinked PVP-$H_2O_2$ complex | 0 | 5.5 | 0 | 5.5 | 0 |
| $H_2O_2$ (35%) | 3.0 | 0 | 3.0 | 0 | 0 |
| SLS | 2.0 | 2 | 2 | 2 | 2.0 |
| Sodium saccharin | 0.5 | 0.5 | 0.5 | 0.5 | 0.5 |
| Sucralose | 0.02 | 0.01 | 0.01 | 0.01 | 0.02 |
| Water | 0 | 0 | 0 | 0 | 0 |

Experimental Example 5. Measurement of Stability of Toothpaste (1) Method of Measuring Stability of Hydrogen Peroxide at High Temperature Over Time According to a titration method of using iodine, which is a method of indirectly measuring a hydrogen peroxide concentration, the hydrogen peroxide concentrations early after preparation of the toothpaste and after storing the toothpaste in the tube for 4 weeks in a 50° C. water bath were measured, and a ratio of the concentration of remaining hydrogen peroxide to the initial concentration of hydrogen peroxide was calculated. When no decomposition occurred, it was expressed as 100%.

(2) Method of Measuring Phase Stability of Toothpaste at High Temperature

After storing the toothpaste in the tube for 4 weeks in a 50° C. water bath, the surface condition was visually observed to examine whether there was any liquid separation when the toothpaste was squeezed, and whether the content of the toothpaste tightly stuck in the tube when the tube was cut in half.

(3) Results of Measuring Stability of Toothpaste

The results of measuring stability of hydrogen peroxide at a high temperature over time and phase stability of the toothpaste at a high temperature with respect to the toothpaste compositions of Examples 10 to 12, 16, and 17 and Comparative Examples 10 to 14 are shown in Table 9 below.

indicating that due to use of the spreading agent, the toothpaste compositions tightly stuck in the tube, and thus water generation due to hydrolysis did not occur to inhibit a phase separation phenomenon, and as a result, the toothpaste composition including hydrogen peroxide and the thickener, in which hydrogen peroxide and the thickener are separated from each other, may have remarkably improved stability of the toothpaste.

Experimental Example 6. Measurement of Sense of Use and Whitening Effect of Toothpaste (1) Method of Measuring Feelings of Refreshment and Cleaning 10 adults were allowed to brush their teeth using the toothpaste compositions of Examples 10 to 17 and Comparative Examples 10 to 15 for 1 minute or more three times a day for 1 month, and then the feelings of refreshment and cleaning were surveyed.

Survey Response Criteria

5: Feelings of refreshment and cleaning are given, like those of toothpastes used before.

4: Both feelings of cleaning and refreshment after use are acceptable.

3: Any one feeling of cleaning and refreshment after use is acceptable.

2: Both feelings of cleaning and refreshment after use are unsatisfactory, even though you do not want to use another toothpaste.

TABLE 9

| Stored at 50° C. | Example 10 | Example 11 | Example 12 | Example 16 | Example 17 | Comparative Example 10 | Comparative Example 11 | Comparative Example 12 | Comparative Example 13 | Comparative Example 14 |
|---|---|---|---|---|---|---|---|---|---|---|
| Residual peroxide ratio (%) after 4 weeks | 90% | 91% | 90% | 91% | 90% | 86% | 88% | 88% | 86% | Not added |
| Toothpaste phase stability in tube after 4 weeks | 5 | 5 | 5 | 4 | 4 | 3 | 1 | 2 | 2 | 3 |

From the results of Table 9, it was confirmed that 90% or more of the peroxide of the toothpaste compositions of Examples 10 to 12, 16, and 17 was not decomposed even after 4 weeks, and the toothpaste compositions of Examples 10 to 12, and 16 were not separated from the tube and tightly stuck in the tube even after 4 weeks, unlike the toothpaste compositions of Comparative Examples 10 to 14 which were separated from the tube after 4 weeks (FIG. 3), 1: Both feelings of cleaning and refreshment after use are very unsatisfactory such that you want to use another toothpaste.

(2) Method of Measuring Stickiness 10 adults were allowed to brush their teeth using the toothpaste compositions of Examples 10 to 17 and Comparative Examples 10 to 15 for 1 minute or more three times a day for 1 month, and then the stickiness was surveyed.

Survey Response Criteria
5: It is not sticky.
4: It is a little sticky, but there is no problem in using it.
3: It is very sticky, but there is no problem in using it.
2: It is too sticky to brush your teeth.
1: It is so sticky that it is uncomfortable to squeeze it on the toothbrush.

(3) Method of Measuring Whitening Effect and Cleaning Power 10 adults were allowed to brush their teeth using the toothpaste compositions of Examples 10 to 17 and Comparative Examples 10 to 15 for 1 minute or more three times a day for 1 month, and then the whitening effect and cleaning power were surveyed.

Survey Response Criteria
5: You feel like the teeth are obviously brightened.
4: You feel like the tooth surface becomes smooth and the teeth are brightened.
3: You feel like the teeth are slightly brightened.
2: You feel like the tooth surface becomes a little clean.
1: You feel no difference in the whitening effect and the feeling of cleaning before and after use.

(4) Method of Measuring In Vitro Tooth Whitening Effect

Artificial teeth (tooth enamel, hydroxyapatite, which is a material primarily constituting dentin) were prepared into tablet specimens, and stained using tooth staining materials such as tea, coffee, mucin, metal salts, etc. Thereafter, the toothpaste was brushed in a slurry state at the actual concentration (25 g/40 mL) 5,400 times at a speed of 90 times per second by using a brushing machine for testing a cleaning power, and the degree of brightness of the stained artificial tooth specimen before and after cleaning was measured using a chromameter, and a color change ($\Delta E$) was calculated.

(5) Results of Measuring Sense of Use and Whitening Effect

1) Results of Measuring Sense of Use

The results of measuring the in vitro tooth whitening effect with respect to the toothpaste compositions of Examples 10 to 17 and Comparative Examples 10 to 15 are shown in Table 10 below.

TABLE 10

|  | Example 10 | Example 11 | Example 12 | Example 13 | Example 14 | Example 15 | Example 16 |
|---|---|---|---|---|---|---|---|
| Feeling of refreshment and cleaning | 5 | 5 | 5 | 5 | 5 | 5 | 5 |
| Stickiness | 5 | 5 | 5 | 5 | 5 | 5 | 5 |
| Whitening effect and Cleaning power | 5 | 5 | 5 | 5 | 5 | 5 | 4 |

|  | Example 17 | Comparative Example 10 | Comparative Example 11 | Comparative Example 12 | Comparative Example 13 | Comparative Example 14 | Comparative Example 15 |
|---|---|---|---|---|---|---|---|
| Feeling of refreshment and cleaning | 2 | 4 | 4 | 2 | 2 | 1 | 1 |
| Stickiness | 1 | 5 | 5 | 1 | 4 | 5 | 5 |
| Whitening effect and Cleaning power | 4 | 4 | 4 | 4 | 3 | 2 | 3 |

From the results of Table 10, it was confirmed that the toothpaste compositions of Examples 10 to 17 provided excellent feelings of cleaning and refreshment, no stickiness, and an excellent whitening effect by remarkably brightening the teeth, as compared with Comparative Examples 10 to 15, indicating that due to the use of crosslinked PVP as the thickener, the toothpaste compositions have no stickiness and improved sense of use.

2) Results of Measuring In Vitro Tooth Whitening Effect

The results of measuring the in vitro tooth whitening effect with respect to the toothpaste compositions of Examples 10 to 12, 16, and 17 and Comparative Examples 11, 13, and 14 are shown in Table 11 below.

TABLE 11

|  | Example 10 | Example 11 | Example 12 | Example 16 | Example 17 | Comparative Example 10 | Comparative Example 11 | Comparative Example 13 | Comparative Example 14 |
|---|---|---|---|---|---|---|---|---|---|
| $\Delta E$ (5400 times) | 26.8 ± 0.44 | 25.9 ± 0.71 | 26.3 ± 0.90 | 21.5 ± 0.57 | 20.8 ± 0.29 | 26.0 ± 1.02 | 20.9 ± 0.25 | 11.5 ± 0.85 | 14.0 ± 1.20 |

From the results of Table 11, it was confirmed that the toothpaste compositions of Examples 10 to 12, 16, and 17, in which hydrogen peroxide and the thickener are separated from each other, exhibited a whitening effect 1.3 to 2.3 times higher than that of the toothpaste compositions of Comparative Examples 11, 13, and 14, in which a complex of hydrogen peroxide and the thickener is included, indicating that the toothpaste compositions including hydrogen peroxide and the thickener, in which hydrogen peroxide and the thickener are separated from each other, may exhibit a much more excellent whitening effect due to remarkably rapid decomposition of hydrogen peroxide when actually used.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the present invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A toothpaste composition comprising silica and a chelating agent including phosphate, wherein the chelating agent is supersaturated to precipitate phosphate and a content of the precipitated phosphate is 2% to 10%, based on the total weight of the toothpaste composition and an average diameter of the precipitated phosphate particles ranges from 75 μm to 180 μm, wherein the chelating agent comprise sodium hexametaphosphate (SHMP).

2. The toothpaste composition of claim 1, wherein the chelating agent further comprises tetrasodium pyrophosphate (TSPP) or sodium acid pyrophosphate (SAPP).

3. The toothpaste composition of claim 1, wherein the silica comprises abrasive silica.

4. The toothpaste composition of claim 1, wherein the toothpaste composition comprises water in an amount of 1% to 10% based on the total weight of the toothpaste composition.

* * * * *